(12) United States Patent
Barraclough

(10) Patent No.: US 11,340,149 B2
(45) Date of Patent: May 24, 2022

(54) SOLVENT COMPOUND FOR A PARTICLE COUNTER/IMAGER AND ASSOCIATED METHOD

(71) Applicant: Spectro Scientific, Inc., Chelmsford, MA (US)

(72) Inventor: Thomas G. Barraclough, Bolton, MA (US)

(73) Assignee: Spectro Scientific, Inc., Chelmsford, MA (US)

( * ) Notice: Subject to any disclaimer, the term of this patent is extended or adjusted under 35 U.S.C. 154(b) by 532 days.

(21) Appl. No.: 16/430,596

(22) Filed: Jun. 4, 2019

(65) Prior Publication Data

US 2019/0368985 A1 Dec. 5, 2019

Related U.S. Application Data

(60) Provisional application No. 62/680,186, filed on Jun. 4, 2018.

(51) Int. Cl.
| | | |
|---|---|---|
| *G01N 1/38* | (2006.01) | |
| *G01N 33/28* | (2006.01) | |
| *G01N 15/02* | (2006.01) | |
| *G01N 1/10* | (2006.01) | |
| *G01N 15/10* | (2006.01) | |

(52) U.S. Cl.
CPC .............. *G01N 1/38* (2013.01); *G01N 1/10* (2013.01); *G01N 15/0227* (2013.01); *G01N 15/10* (2013.01); *G01N 33/2835* (2013.01); *G01N 2001/386* (2013.01); *G01N 2015/1062* (2013.01)

(58) Field of Classification Search
CPC ........... G01N 1/10; G01N 3815/02278; G01N 3815/10; B01L 13/00
See application file for complete search history.

(56) References Cited

U.S. PATENT DOCUMENTS

| | | | |
|---|---|---|---|
| 6,064,480 A | 5/2000 | Mountain et al. | |
| 9,274,041 B2 | 3/2016 | Henning et al. | |
| 2017/0321505 A1* | 11/2017 | Murphy | .................. E21B 21/01 |

FOREIGN PATENT DOCUMENTS

EP        1715323 A1    10/2006

\* cited by examiner

*Primary Examiner* — Jennifer Wecker
*Assistant Examiner* — Kathryn Elizabeth Limbaugh
(74) *Attorney, Agent, or Firm* — Iandiorio Teska & Coleman, LLP

(57) ABSTRACT

A solvent compound for a particle counter/imager system, the solvent compound includes a liquid solvent miscible with oil to remove oil from the particle counter/imager system and a liquid dispersive surfactant configured to break large water droplets into smaller droplets less than a predetermined size. The liquid dispersive surfactant is miscible with the solvent and is nontoxic and nonflammable.

14 Claims, 3 Drawing Sheets

SOLVENT COMPOUND FOR A PARTICLE COUNTER/IMAGER AND ASSOCIATED METHOD

RELATED APPLICATIONS

This application claims benefit of and priority to U.S. Provisional Application Ser. No. 62/680,186 filed Jun. 4, 2018, under 35 U.S.C. §§ 119, 120, 363, 365, and 37 C.F.R. § 1.55 and § 1.78, which is incorporated herein by this reference.

FIELD OF THE INVENTION

The invention relates to a solvent compound for cleaning a particle counter/imager systems between tests of fluid (e.g., oil) samples.

BACKGROUND OF THE INVENTION

Particle counter and wear classification systems are used to analyze fluids (e.g., oil) used in various machinery or assets (e.g., engines, pumps, gear boxes, and the like). Oil, for example, is taken from a machine (eg. from the sump) and placed in a bottle. A pump is used to draw the oil out of the vial and to deliver the oil to a flow cell of an imaging subsystem. Radiation is directed through the flow cell and imaged by a CCD camera. In this way, images of any wear particles in the oil are produced and software can be used to analyze the images and count the number of particles detected above a predetermined size (e.g., 20 microns) and to classify the particles (e.g., cutting, sliding, fatigue, nonmetallic, and water) based on the size and shape of the particles detected. See, for example, U.S. Pat. No. 9,274,041 incorporated herein by this reference.

Between uses, the system must be cleaned with a suitable non-polar oil dissolving solvent to quickly remove the oil from the system to prevent cross contamination of oil from one sample with oil from another sample. Often, however, water contamination in the oil samples remains in the system, for example, in the flow cell and the tubing leading to and from the flow cell. The high surface tension of water due to its polar nature forms droplets on the flow cell and tubing surfaces and remains stuck in the system. Acetone and alcohols must then be used to clean the system out and some solvents used are toxic, flammable, and thus not shippable, and/or can degrade the components of the system including the sample cell and tubing.

When another oil sample is tested, any leftover water droplets, when imaged, appear to the system as wear particles. Thus, the system will report an erroneous number of particles, incorrect particle size distributions, and/or incorrect particle shape classifications.

One method for correcting this problem is delineated in ASTM D7647-10 (U.S. Pat. No. 6,064,480) incorporated herein by this reference. The particle counts contributed by the presence of water in the system is negated by diluting the oil with a solvent mixture prior to testing. The flammability and toxicity of the chemical mixture used in ASTM D7647 does not lend itself as a suitable routine flushing solvent to remove water already present in optical particle counter systems. The solvent mixture described in this patent has been designed as a safe, non flammable, non toxic routine oil flushing solvent with water removal capability. The solvent can also be used as a pre-sample analysis water masking solvent to dilute samples with up to 1200 ppm free water in the ratios described in ASTM D7647. Larger diluent ratios in the solvent or with sample will result in higher free water masking capability.

SUMMARY OF THE INVENTION

Featured is a new solvent compound for a particle counter/wear classification system which removes oil from the system between uses and which also breaks up large water droplets into smaller droplets less than, for example, 4 microns in size so the imaging system does not detect them. The smaller water droplets may also be successfully flushed out of the system by the solvent compound. At the same time, the solvent compound is not toxic and nonflammable. The solvent component also does not harm the flow cell or the tubing of the imaging system.

In one aspect, a solvent compound for a particle counter/imager system is featured. The solvent compound includes a liquid solvent miscible with oil to remove oil from the particle counter/imager system and a liquid dispersive surfactant configured to break large water droplets into smaller droplets less than a predetermined size, the liquid dispersive surfactant miscible with the solvent, nontoxic, and nonflammable.

In one embodiment, a volume of the liquid solvent in the compound may be in the range of about 16% to about 99% and a volume of the liquid dispersive surfactant in the compound may be in the range of about 1% to about 15%. The volume of the liquid solvent in the compound may be about 97.5% and the volume of the liquid dispersive surfactant in the compound may be about 2.5%. The liquid solvent may comprise hydrotreated isoparaffins and naphthenics. The liquid dispersive surfactant may comprise Octylphenol Ethoxlate. The liquid dispersive surfactant may be configured to break the large water droplets having a size greater than about 20 microns into smaller particles having a size less than about 20 microns. The liquid dispersive surfactant may be configured to break large water droplets having a size greater than about 20 microns into smaller droplets having a size less than about 4 microns.

In another aspect, a method of testing an oil sample is featured. The method includes urging a first oil sample through an imaging subsystem to image any particles in the first oil sample, count any particles in the first oil sample above a predetermined size, and/or classify any particles in the first oil sample. A solvent compound comprising a liquid solvent miscible with oil to remove oil from the imaging subsystem and a liquid dispersive surfactant configured to break large water droplets in the imaging subsystem into smaller droplets less than said predetermined size is obtained. The liquid dispersive surfactant is preferably miscible with the solvent and is nontoxic and nonflammable. The solvent compound is urged through the imaging subsystem to remove any traces of the first oil sample therein and to break any water droplets present in the imaging subsystem into smaller water droplets less than said predetermined size. A second oil sample is urged through the imaging subsystem to image any particles present in the second oil sample, count any particles in the second oil sample above the predetermined size, and/or classify any particles in the second oil sample above said predetermined size.

In one embodiment, the method may include providing the solvent compound by mixing about 16% to about 99% by volume of the liquid solvent with about 1% to about 15% by volume of the liquid dispersive surfactant. The method may further include providing the solvent compound by mixing about 97.5% by volume of the liquid solvent with about 2.5% by volume of the liquid dispersive surfactant. Providing the solvent may include mixing about 16% to about 99% by volume hydrotreated isoparaffins and naphthenics with about 1% to about 15% by volume Octylphenol Ethoxlate. Providing the solvent may include mixing about 97.5% by volume hydrotreated isoparaffins and naphthenics with about 2.5% by volume Octylphenol Ethoxlate. The liquid dispersive surfactant may be configured to break the large water droplets having a size greater than about 20 microns into smaller particles having a size less than about 20 microns. The liquid dispersive surfactant may be configured to break the large water droplets having a size greater than about 20 microns into smaller droplets having a size less than about 4 microns.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
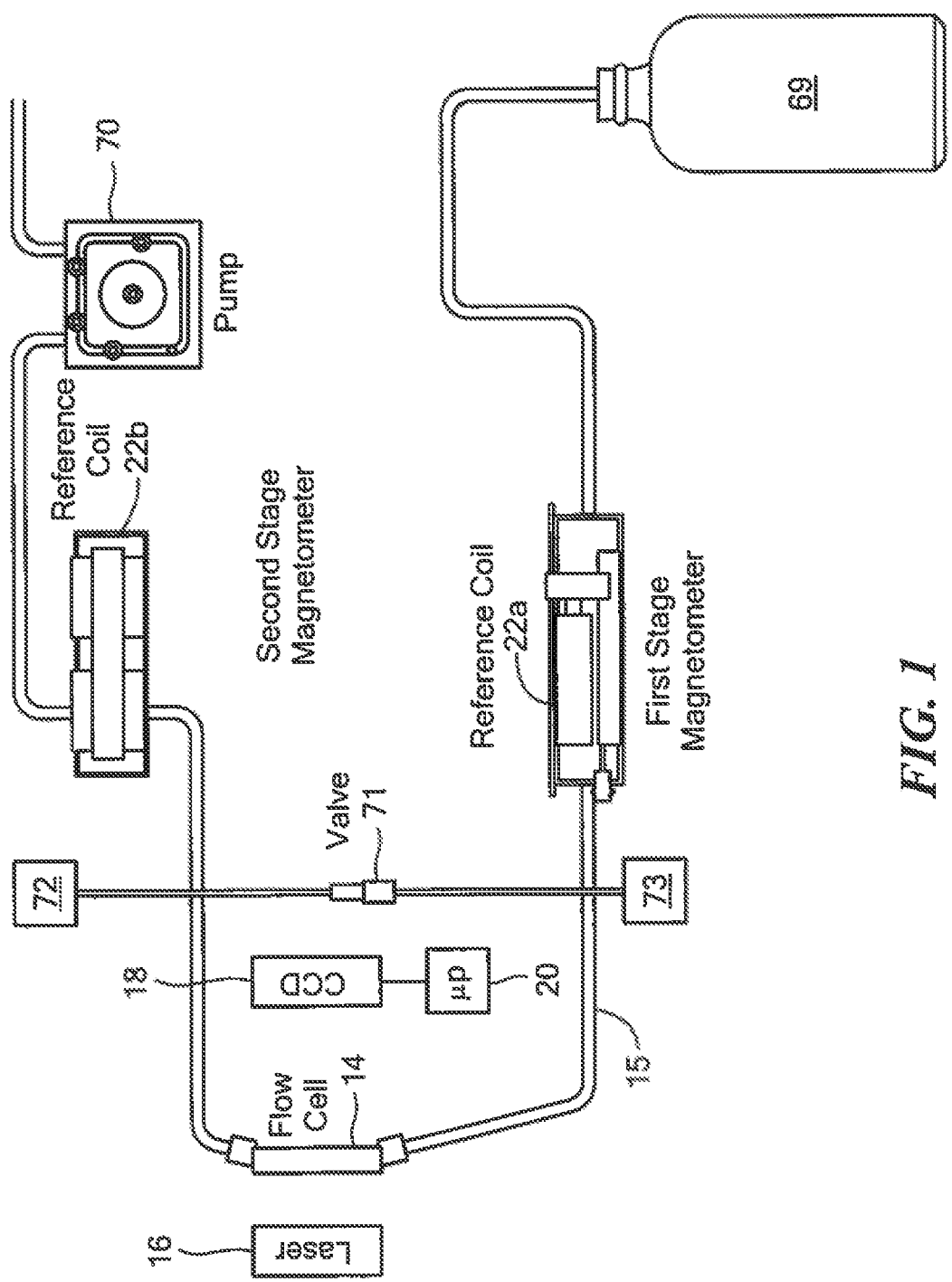
FIG. 1 is a schematic view showing one example of one embodiment of a particle counter/wear classification system.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows how fluid from a sample bottle 69 may be urged by pump 70 through first stage magnetometer 22a, flow cell 14, and second stage magnetometer 22b. A valve 71 may be activated by pressure sensor 72, 73 when needed, typically to bypass the high flow restriction flow cell 14 for optimal cleaning. For the imaging subsystem, a laser 16 directs electromagnetic radiation through sample cell 14 and detector 18 (including, for example, a CCD imager) images the contents of the cell. Electronic signals output by detector 18 concerning the number, size, and shape of particles in the fluid is processed by a processor subsystem 20 responsive to detector 18. Processor subsystem 20 may be a computer, a microprocessor based electronic subsystem, a field programmable gate array appropriately programmed, an application specific integrated circuit, or the like. The imaging subsystem is configured (using optical devices if necessary) to focus appropriately on certain size particles of interest, typically between 20 and 100 microns. The imaging subsystem, for certain particle size ranges, can detect the particles, determine their size, determine their morphology (shape), and processor subsystem 20 can include algorithms to categorize the particles (for example, particles generated by cutting wear, particles generated by sliding wear, and the like).

As noted above, the conventional cleaning method involves the use of a solvent placed in bottle 69 and pumped through the system. This cleaning method is typically carried out as between testing of different oil samples. Some solvents, however, are toxic and many are flammable and thus not shippable. Furthermore, some solvents can degrade components of the system, for example, the flow cell 14 and tubing 15. And, water droplets greater than 4 microns in size may remain in flow cell 14 and/or tubing 15 and are then detected by CCD camera 18 when another oil sample is tested resulting in erroneous readings and measurements. The ASTM D7647-10 method requires dilution of the oil sample and results in extra steps in order to test oil samples. Moreover, some users of the system may not be familiar with this standardized method and/or may not have the necessary experience with it to carry out the ASTM method properly.

In one example, a new solvent compound in accordance with one or more embodiments of this invention is placed in bottle 69 between uses of the system to both remove the oil in tubing 15 and flow cell 14 and to break any water droplets therein into smaller water droplets preferably less than about 4 microns in size. These smaller water droplets are then either flushed out of the system with the solvent compound or, if any remain, they are not imaged by CCD camera 18 and thus do not result in erroneous readings.

The solvent compound preferably includes a liquid solvent miscible with oil to remove oil from the particle counter/imager system and a liquid dispersive surfactant configured to break large water droplets into smaller droplets less than 20 microns in size. In one example, the liquid dispersive surfactant broke large particles above 20 microns in size to particles less than about 4 microns in size. The liquid dispersive surfactant is preferably miscible with the solvent, is nontoxic, and nonflammable. In one example, the volume of liquid solvent in the compound is in the range of about 16% to about 99% and the volume of the liquid dispersive surfactant in the compound is in the range of about 1% to about 15%. In another example, the volume of the liquid solvent in the compound is preferably approximately or about 97.5% and the volume of the liquid dispersive surfactant in the compound is approximately or about 2.5%. In one example, the solvent comprises hydrotreated isoparaffins and naphthenics. In another example, the solvent compound may be provided by mixing about 16% to about 99% hydrotreated isoparaffins and naphthenics with about 1% to about 15% by volume Octylphenol Ethoxlate. In yet another example, providing the solvent may include mixing about 95.7% by volume hydrotreated isoparaffins and naphthenics with about 2.5% by volume Octylphenol Ethoxlate. In one example, the liquid dispersive surfactant is Octylphenol Ethoxlate (Dow Chemical Corp. sold under the trade name Triton X-45 Surfactant). In some embodiments, 55 gallons of hydrotreated isoparaffins and naphthenics are mixed with approximately 1.41 gallons of Octylphenol Ethoxlate using a paddle stirrer. In testing, the liquid dispersive surfactant remains soluble in hydrotreated isoparaffins and naphthenics for 18 months resulting in a fairly long shelf life. The solvent solution (the hydrotreated isoparaffins and naphthenics and the surfactant) does not react with hydrocarbon oils creating interference in the counts and is not soluble in water. The surfactant used is a nonionic water-in-oil emulsifier (not soluble in water) but dispersible in water. The nonionic surfactant is preferably soluble in a 39:1 hydrotreated isoparaffins and naphthenics mixture. The nonionic surfactant preferably has a Hydrophile-Lipophile Balance (HLB) of 9.8 which makes it a water-in-oil (w/o) emulsifier (i.e., water is dispersed in the continuous oil phase). All HLB's<10 make the surfactants w/o emulsifiers, and HLB's>10 make them oil-in-water emulsifiers (o/w emulsifier).

Figure 2:
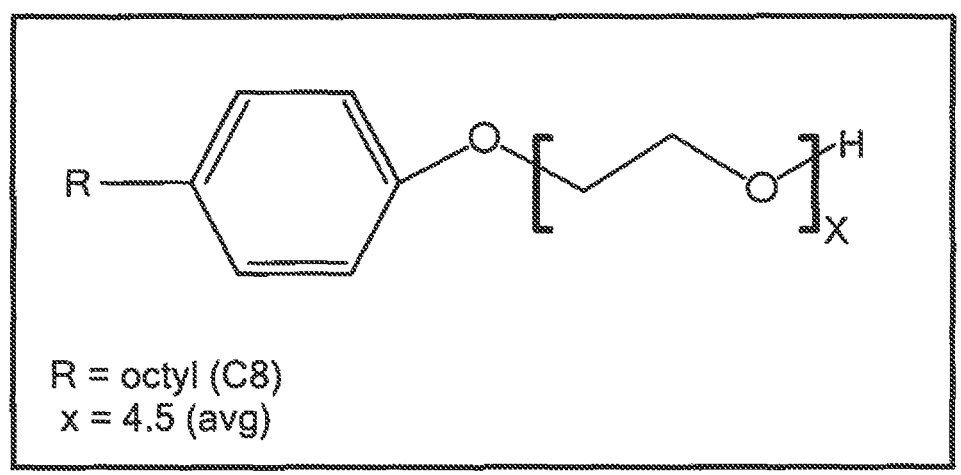
FIG. 2 is a view showing the chemical structure of an exemplary liquid dispersive surfactant used as a component of the solvent compound described herein.

The surfactant molecules preferably have a water-compatible (Hydrophilic) polar end and an Oil-compatible (lipophilic) non-polar end. FIG. 2 shows the chemical structure of an exemplary liquid dispersive surfactant used as a component of the solvent compound discussed above. When oil samples containing water are pre-diluted with this mixture, because the surfactant is soluble in hydrotreated isoparaffins and naphthenics, it enables these core ingredients to be able to penetrate through the oil via the hydrotreated isoparaffins and naphthenics due to its solubility and get to the water/oil interface. The surfactant then reduces the surface tension between the oil and water by orientating the hydrophilic groups with the water phase and the hydrophobic groups with the oil. This is how the larger interfering water droplets are then broken down into smaller droplets, dispersed into the oil, and not seen by the CCD (<4 um) particle imager. The same happens with water left over from a sample in the device. During the flush of the system, the surface tension created at the water/oil/device material interface is broken down and the larger droplets are broken into smaller droplets and carried away by the solvent leaving a perfectly clean system.

In use, a first oil sample in bottle 69, FIG. 1 is urged via tubing 15 and pump 70 through first stage magnetometer 22a, flow cell 14, and second stage magnetometer 22b whereupon the imaging subsystem images any particles in the oil, counts any particles in the oil sample above a predetermined size, and/or classifies the particles as discussed above.

Next, the solvent compound described above is urged through the imaging subsystem including tubing 15 and flow cell 14 to remove any traces of the first oil sample therein and to break any water droplets present in the imaging subsystem into smaller water droplets less than the predetermined size the imaging subsystem can count and/or to flush those smaller water droplets in tubing 15 and flow cell 14 out of the system. Next, a second oil sample in bottle 69 is urged through the imaging subsystem to image any particles in the second oil sample, to count any particles in the second oil sample above the predetermined size, and/or to classify any particles in the second oil sample.

Figure 3:
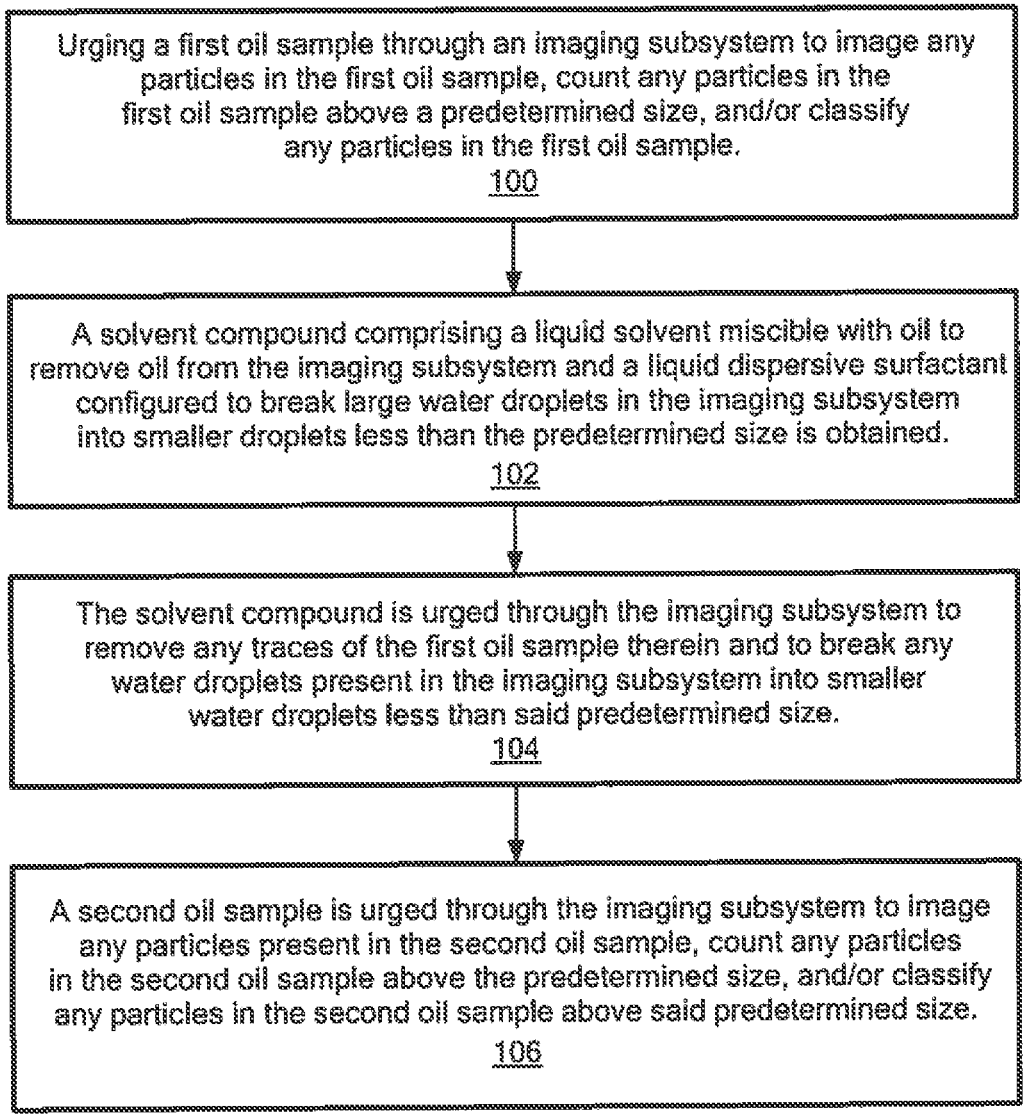
FIG. 3 is a block diagram showing the primary steps of one embodiment of the method of testing an oil system in accordance with this invention.

One example of the method of testing an oil sample of one or more embodiments of this invention includes urging a first sample through an imaging subsystem to image any particles in the first oil sample, count all particles in the first oil sample above a predetermined size, and/or classify the particles in the first oil sample, step 100, FIG. 3. A solvent compound comprising a liquid solvent miscible with oil to remove water from the imaging subsystem and a liquid dispersive surfactant configured to break large water droplets in the imaging system into smaller droplets less than a predetermined size is obtained, step 102. The liquid dispersive surfactant is preferably miscible with the solvent and is preferably non-toxic and non-flammable. The solvent compound is urged through the imaging system to remove any traces of the first oil sample therein and to break any water droplets present in the imaging system into smaller water droplets less than the predetermined size, step 104. A second oil sample is urged through the imaging system to image any particles present in the second oil sample, count any particles in the second oil sample above the predetermined size, and/or classify any particles in the second oil sample above the predetermined size, step 106. The method may include providing a solvent compound by mixing about 16% to about 99% by volume of the liquid solvent with about 1% to about 15% by volume of the liquid dispersive surfactant. The method may include providing the solvent by mixing about 97.5% by volume of the liquid solvent with about 2.5% by volume of the liquid dispersive surfactant. The method may include providing the by mixing about 16% to about 99% by volume hydrotreated isoparaffins and naphthenics with about 1% to about 15% by volume Octyphenol Ethoxlate. The method may include providing the solvent by mixing about 97.5% by volume hydrotreated isoparaffins and naphthenics with about 2.5% by volume Octyphenol Ethoxlate. The liquid dispersive be configured to break the large water droplets having a size greater than about 20 microns into smaller particles having a size less than about 20 microns. The liquid dispersive may be configured to break the large water droplets having a size greater than about 20 microns into smaller particles having a size less than about 4 microns.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A solvent compound for a particle counter/imager system, the solvent compound comprising:
    a liquid solvent miscible with oil to remove oil from the particle counter/imager system; and
    a liquid dispersive surfactant configured to break large water droplets into smaller droplets less than a predetermined size, the liquid dispersive surfactant miscible with the solvent, nontoxic, and nonflammable.

2. The solvent compound of claim 1 in which a volume of the liquid solvent in the compound is in the range of about 16% to about 99% and a volume of the liquid dispersive surfactant in the compound is in the range of about 1% to about 15%.

3. The solvent compound of claim 2 in which the volume of the liquid solvent in the compound is about 97.5% and the volume of the liquid dispersive surfactant in the compound is about 2.5%.

4. The solvent compound of claim 1 in which the liquid solvent comprises hydrotreated isoparaffins and naphthenics.

5. The solvent compound of claim 1 in which the liquid dispersive surfactant comprises Octylphenol Ethoxlate.

6. The solvent compound of claim 1 in which the liquid dispersive surfactant is configured to break the large water droplets having a size greater than about 20 microns into smaller particles having a size less than about 20 microns.

7. The solvent compound of claim 6 in which the liquid dispersive surfactant is configured to break large water droplets having a size greater than about 20 microns into smaller droplets having a size less than about 4 microns.

8. A method of testing an oil sample, the method comprising:
   urging a first oil sample through an imaging subsystem to image any particles in the first oil sample, count any particles in the first oil sample above a predetermined size, and/or classify any particles in the first oil sample;
   obtaining a solvent compound comprising a liquid solvent miscible with oil to remove oil from the imaging subsystem and a liquid dispersive surfactant configured to break large water droplets in the imaging subsystem into smaller droplets less than said predetermined size, the liquid dispersive surfactant miscible with the solvent, nontoxic, and nonflammable;
   urging the solvent compound through the imaging subsystem to remove any traces of the first oil sample therein and to break any water droplets present in the imaging subsystem into smaller water droplets less than said predetermined size; and
   urging a second oil sample through the imaging subsystem to image any particles present in the second oil sample, count any particles in the second oil sample above the predetermined size, and/or classify any particles in the second oil sample above said predetermined size.

9. The method of claim 8 further including providing the solvent compound by mixing about 16% to about 99% by volume of the liquid solvent with about 1% to about 15% by volume of the liquid dispersive surfactant.

10. The method of claim 9 further including providing the solvent compound by mixing about 97.5% by volume of the liquid solvent with about 2.5% by volume of the liquid dispersive surfactant.

11. The method of claim 1 in which providing the solvent includes mixing about 16% to about 99% by volume hydrotreated isoparaffins and naphthenics with about 1% to about 15% by volume Octylphenol Ethoxlate.

12. The method of claim 11 in which providing the solvent includes mixing about 97.5% by volume hydrotreated isoparaffins and naphthenics with about 2.5% by volume Octylphenol Ethoxlate.

13. The method of claim 8 in which the liquid dispersive surfactant is configured to break the large water droplets having a size greater than about 20 microns into smaller particles having a size less than about 20 microns.

14. The method of claim 13 in which the liquid dispersive surfactant is configured to break the large water droplets having a size greater than about 20 microns into smaller droplets having a size less than about 4 microns.

* * * * *